(12) United States Patent
Dodds et al.

(10) Patent No.: US 11,877,872 B1
(45) Date of Patent: Jan. 23, 2024

(54) VITAL SIGNS MONITOR CABLE RETRACTION SYSTEM

(71) Applicant: James Cameron Dodds, Greenville, SC (US)

(72) Inventors: James Cameron Dodds, Greenville, SC (US); Lisa Fitzgerald, Leesburg, FL (US)

(73) Assignee: James Cameron Dodds, Greenville, SC (US)

( * ) Notice: Subject to any disclaimer, the term of this patent is extended or adjusted under 35 U.S.C. 154(b) by 0 days.

(21) Appl. No.: 18/221,570

(22) Filed: Jul. 13, 2023

Related U.S. Application Data

(60) Provisional application No. 63/462,063, filed on Apr. 26, 2023.

(51) Int. Cl.
*A61B 50/20* (2016.01)
(52) U.S. Cl.
CPC .................................. *A61B 50/20* (2016.02)
(58) Field of Classification Search
CPC ...................................................... A61B 50/20
USPC ............................................................ 206/349
See application file for complete search history.

(56) References Cited

U.S. PATENT DOCUMENTS

| | | | | |
|---|---|---|---|---|
| 5,435,979 A * | 7/1995 | Miller | ...................... | A61C 3/04 211/60.1 |
| 2012/0193372 A1* | 8/2012 | Coggins | .................. | A61B 50/20 242/564 |
| 2016/0089204 A1* | 3/2016 | Chow | .................... | A61M 25/02 224/217 |
| 2016/0242862 A1* | 8/2016 | Chow | .............. | A61B 17/06061 |

* cited by examiner

*Primary Examiner* — Jacob K Ackun
(74) *Attorney, Agent, or Firm* — Shumaker, Loop & Kendrick, LLP

(57) ABSTRACT

A cable retraction system, useful at least in vital signs monitoring systems, rolls sensors cables and tubes on rotary spring spools, inside a protective enclosure, for storage. The cables and tubes along with the sensors can easily be pulled out for use and then retracted back into the enclosure as required. This eliminates tangled cables and tubes and provides protection for the sensors by not being on dangling long cables when not in use.

18 Claims, 13 Drawing Sheets

VITAL SIGNS MONITOR CABLE RETRACTION SYSTEM

CROSS-REFERENCE TO RELATED APPLICATION

This application claims the benefit of priority of U.S. provisional patent application No. 63/462,063 titled "Vital Signs Monitor Cable Retraction System," filed on Apr. 26, 2023, which is incorporated herein in its entirety by this reference.

TECHNICAL FIELD

The present invention relates generally to the field of spring-driven retraction spools for cables, wiring and tubes, and more particularly, to multi-line spring-driven retraction devices for medical devices.

BACKGROUND

The vital sign monitor is used by hospitals, clinics, and ambulances to monitor a patient's vital signs that typically include measurement of blood pressure, oxygen saturation, pulse, EKG, and temperature. Each of these measurements require a sensor connected to a cable or tube, from the sensor to the monitor, where results can be displayed on a screen. In a typical setting, these cables and tubes can become tangled and, left un-stored, can be damaged. The sensors can fail to the floor where damage may occur. This condition places a burden on the clinical staff that is under time constraints to monitor vital signs of a patient and is then required to untangle cords or replace sensors. Historically these sensors and cables were draped over the monitor or placed in a basket below the monitor. In both cases this would not guarantee that tangles may occur and un-secured sensors may be damaged.

A need exists to provide better handling of the cables, tubes and sensors that solves the above-mentioned problems.

SUMMARY

This summary is provided to briefly introduce concepts that are further described in the following detailed descriptions. This summary is not intended to identify key features or essential features of the claimed subject matter, nor is it to be construed as limiting the scope of the claimed subject matter.

A retraction system according to at least one embodiment includes: multiple spool assemblies; and an enclosure at least partially housing the spool assemblies. Each spool assembly includes at least one cable or tube, a spool rotationally biased by a spring force, the at least one cable or tube mounted on the spool in a variably wound condition such that, as the cable or tubing is extended, the spool is rotated in a first rotational direction against the spring force. A ratcheting stop is coupled to the spool selectively preventing rotation of the spool in a second rotational direction opposite the first rotational direction thereby selectively preventing retraction of the cable or tubing. A lever attached to the enclosure selectively releases the ratcheting stop to allow the spool to rotate in the second rotational direction by the spring force thereby selectively permitting retraction of the cable or tubing by rewinding at least a portion thereof onto the spool.

In some examples, an interface on a bottom of the enclosure provides a mount point for a pole or wall bracket to be attached.

The enclosure may include a top cover, a rear panel and a bottom mainframe.

The enclosure may include a plurality of apertures for cables or tubing to extend from the spools.

Each spool assembly may further include a spool axle and a rotary spring providing the spring force.

In some examples, at least one cable or tube facilitates medical vital sign monitoring, such as blood pressure, pulse, oxygen level, a EKG signal, and/or temperature.

In at least one embodiment, a spooled line handling system includes multiple spool assemblies spaced along a common axis, and a mainframe at least on which the spool assemblies are mounted. Each one of the multiple spool assemblies includes a respective flexible line, and a spool rotationally biased by a spring torque, the respective flexible line mounted on the spool in a variably wound condition such that, as the respective flexible line is extended by unwinding from the spool, the spool is rotated in a first rotational direction against the spring torque around the common axis of the multiple spool assemblies. A stop device is coupled to the spool selectively preventing rotation of the spool in a second rotational direction opposite the first rotational direction thereby selectively preventing, by opposing the spring torque, retraction of the respective flexible line by winding onto the spool. A release device is movably attached to the mainframe and operatively coupled to the stop device. Upon user action on the release device, the release device selectively releases the stop device to allow the spool to rotate in the second rotational direction by the spring torque thereby selectively permitting retraction of the respective flexible line by rewinding at least a portion thereof onto the spool.

The respective flexible line of at least one of the multiple spool assemblies may include a cable having at least one electrically conducting wire; and, the respective flexible line of at least one other of said multiple spool assemblies may include a tube.

At least one sensor may be connected to the at least one electrically conducting wire, the sensor including or being at least one of an EKG pad, an oxygen sensor, a pulse sensor, and a temperature sensor.

The at least one electrically conducting wire may further be electrically coupled to a vital signs monitor via an electrically conducting slip ring assembly.

A blood pressure cuff may be connected to the tube.

A rotary air joint may be connected to the tube opposite the blood pressure cuff; and an air fitting may have a first end coupled to the tube via the rotary air joint and a second end coupled directly or indirectly to a vital signs monitor.

Each of the multiple spool assemblies may further include a non-rotating axle race affixed to the main frame and retained by the spool.

Friction between the spool and the axle race may oppose the spring torque thereby damping a rotational speed of the spool at least when the spool rotates in the second rotational direction by the spring torque.

The spooled line handling system may further include, each in one-to-one correspondence with a respective one of the multiple spool assemblies a non-rotating cradle connected to the mainframe, and a non-rotating clamp connected at least in part to the cradle by at least one fastener. The cradle and clamp together may define a capture hole in which an engagement portion of the axle race is fixedly captured thereby affixing the axle race to the main frame. The spool may rotate relative to the axle race when the spool is rotated.

The engagement portion of the axle race may include a radially outward facing cylindrical portion and a registration ring. The cradle and clamp may each define a respective radially inward facing arcuate wall, the arcuate wall of the cradle and arcuate wall of the clamp together defining the capture hole. The arcuate wall of the cradle and arcuate wall of the clamp may each define a respective arcuate groove; and the arcuate groove of the clamp and the arcuate groove of the cradle may together define a registration groove in which the registration ring is captured.

Each one of the multiple spool assemblies may include a spring torsionally coupling the spool to the axle race, the spring providing said spring torque.

Each spool may include: a cylinder defining an engagement surface on which the respective flexible line is mounted on the spool in the variably wound condition; and a first flange affixed to the cylinder and extending radially outward from the cylinder for maintaining the flexible line on the spool in the variably wound condition. The cylinder of each spool may have a center axis defined by the common axis.

Each spool may further include: a ring connected to the first flange; and locking teeth extending from the ring radially inward toward the common axis, the locking teeth engaging the stop device when the stop device prevents rotation of the spool in the second rotational direction.

The stop device may include ratchet teeth for engaging the locking teeth, and may be biased to engage the ratchet teeth with the locking teeth. Upon user action on the release device, the release device may move the stop device thereby disengaging the ratchet teeth from the locking teeth.

The release device may include a pivotable lever having an aperture through which the respective flexible line extends.

A cover may be attached to the mainframe, the mainframe and cover together defining an enclosure in which the multiple spool assemblies may be housed.

The cover may include, each in one-to-one correspondence with a respective one of the multiple spool assemblies, a lever well at least partially receiving the pivotable lever.

The cover may include a rear panel from which rearward flexible leads extend, each in one-to-one correspondence with a respective one of the multiple spool assemblies, to couple the respective flexible lines to a vital signs monitor.

The above summary is to be understood as cumulative and inclusive. The above described embodiments and features are combined in various combinations in whole or in part in one or more other embodiments.

BRIEF DESCRIPTION OF THE DRAWINGS

The previous summary and the following detailed descriptions are to be read in view of the drawings, which illustrate some, but not all, embodiments and features as briefly described below. The summary and detailed descriptions, however, are not limited to only those embodiments and features explicitly illustrated.

DETAILED DESCRIPTIONS

Figure 1:
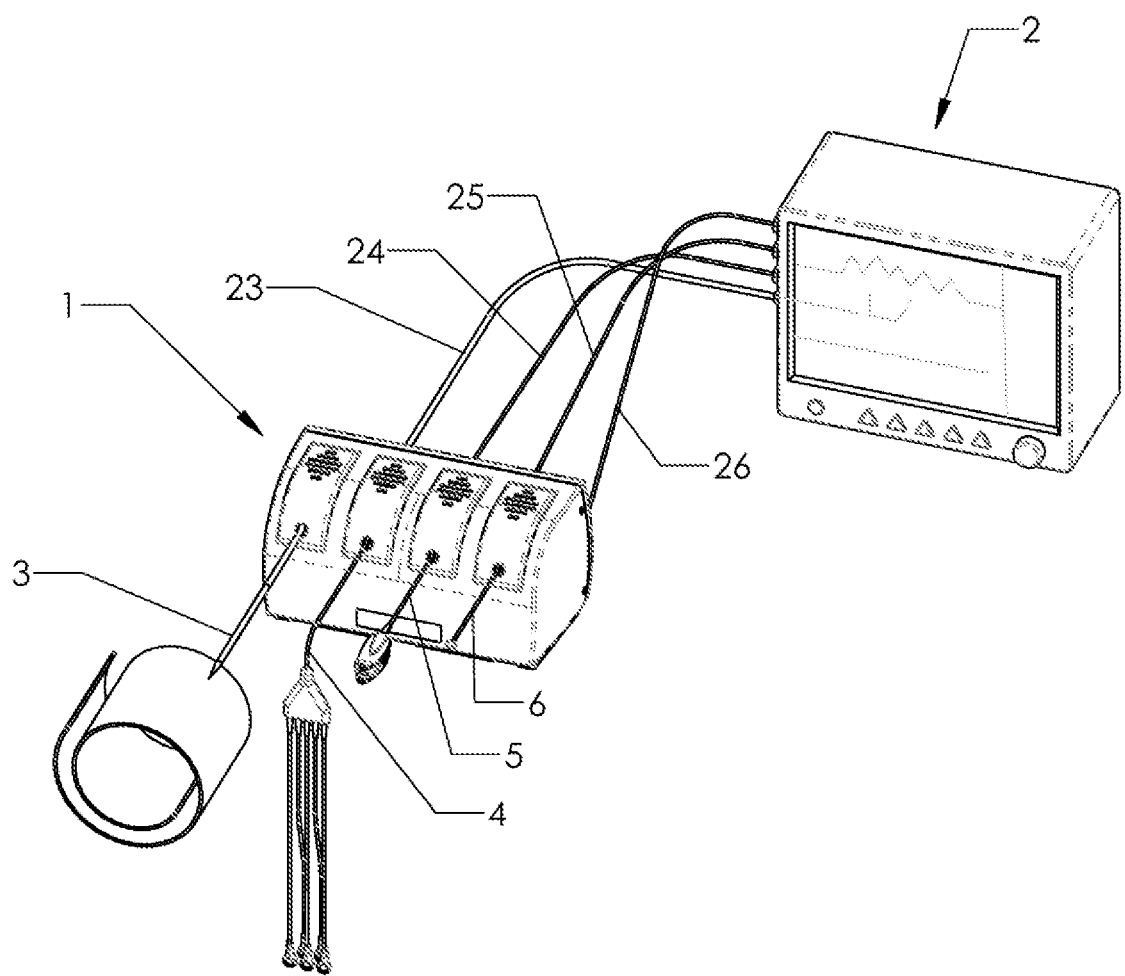
FIG. 1 is a perspective view of the full assembly of a cable retract system according to at least one embodiment, shown with attached medical devices extending forward and a vital signs monitor rearward.
Figure 2:
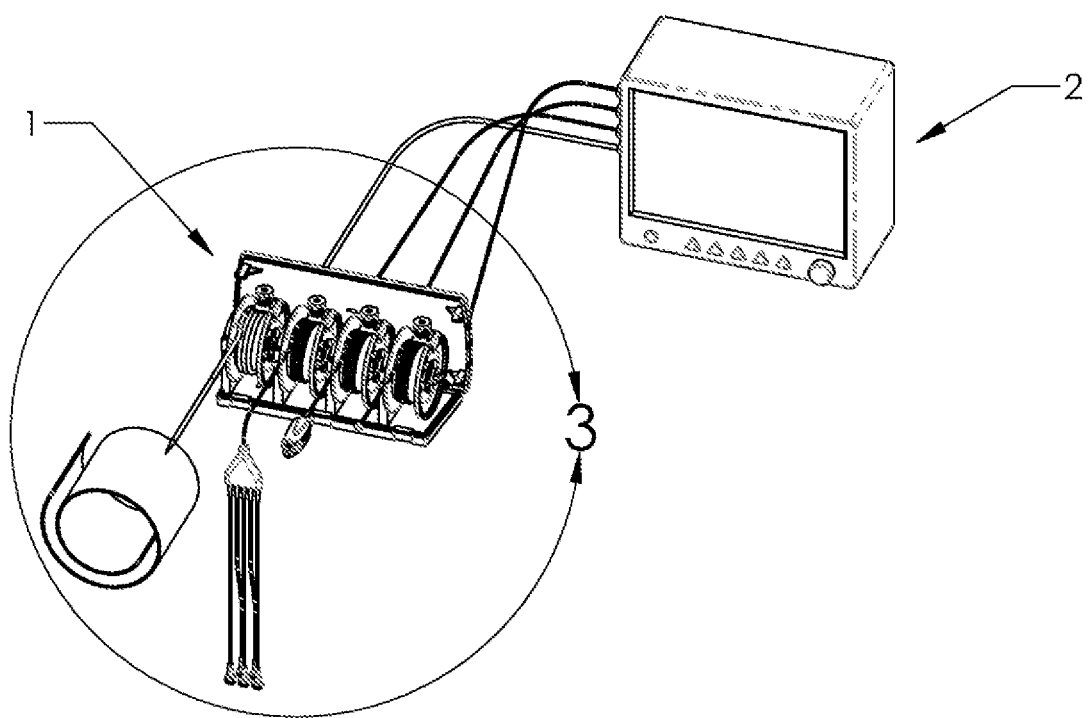
FIG. 2 is a perspective view of the cable retract system of FIG. 1 with the cover removed.

The present invention will now be described more fully, hereinafter with reference to the accompanying drawings in Which exemplary embodiments of the invention are shown. However, the invention may be embodied in many different forms and should not be construed as limited to the representative embodiments set forth herein. The exemplary embodiments are provided so that this disclosure will be both thorough and complete and will fully convey the scope of the invention and enable one of ordinary skill in the art to make, use and practice the invention. Like reference numbers refer to like elements throughout the various drawings.

The present invention will now be described more fully hereinafter with reference to the accompanying drawings in which exemplary embodiments of the invention are shown. However, the invention may be embodied in many different forms, and should not be construed as limited to the representative embodiments set forth herein. The exemplary embodiments are provided so that this disclosure will be both thorough and complete and will fully convey the scope of the invention and enable one of ordinary skill in the art to make, use and practice the invention.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Like reference numbers used throughout the drawings depict like or similar elements. Unless described or implied as exclusive alternatives, features throughout the drawings and descriptions should be taken as cumulative, such that features expressly associated with some particular embodiments can be combined with other embodiments.

Unless defined otherwise, technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a," "an," and "the" refer to "one or more" when used in the subject specification, including the claims.

These descriptions and the referenced drawings specifically disclose a Vital Signs Monitor Cable Retraction System that provides a means to store the cables and tubes on spools that can be pulled out for use and then retracted back on the spools, by means of rotational springs, when not needed. Uses other than that described with reference to vital signs monitoring are within the scope of these descriptions and drawings.

The Vital Sign Monitor Cable Retract System, in the illustrated and/or described embodiment(s), includes spool assemblies in an enclosure that allows cables and tubes to be wound fully retracted into the enclosure. This organizes the cables or tubing, prevents tangles and provides protection for the sensor assemblies by being hung high off the floor. In this embodiment, there are four spools, one for blood pressure, oxygen saturation/pulse, EKG, and temperature. In other embodiments, the number of spool assemblies can vary as the requirement for sensors dictate.

Each spool assembly consists of a spool that is rotationally biased by a spring in a partially wound condition thereby retracting the cable or tubing on the spool. As the cable or tubing is extended, further biasing the spring, a ratcheting stop device prevents retraction of the cable or tubing. A lever for each spool assembly, attached to the enclosure, releases the ratchet to allow the spool to rewind the sensor cable or tubing. To prevent twisting of the cable, a slip-ring assembly is mounted to each cable spool coincident to the center axis. To prevent twisting of the tubing, an air rotational fitting is mounted to the tubing spool coincidental to the center axis. The output of the slip-ring and air rotational fitting transverses through apertures in the rear panel of the enclosure and plugs into the vital signs monitor. A screw boss interface on the bottom of the enclosure provides a mount point for a pole or wall bracket (not shown) to be attached.

Additional features, aspects and advantages of the invention will be set forth in the detailed description which follows, and in part will be readily apparent to those skilled in the art from that description or recognized by practicing the invention as described herein. It should be understood that both the foregoing general description and the following detailed description present various embodiments of the invention and are intended to provide an overview or framework for understanding the nature and character of the invention as it is claimed. The accompanying drawings are included to provide a further understanding of the invention and are incorporated in and constitute a part of this specification.

Referring to FIGS. 1, 2, 3, 4, 5, 6, 7, 8, 9, 10, 11 and 16, the Vital Signs Monitor Cable Retraction System includes, in the illustrated embodiment, a cable retraction device 1 containing four spool assemblies, the blood pressure hose spool assembly 8, the EKG cable spool assembly 9, the oxygen/pulse cable spool assembly 10 and the temperature cable spool assembly 11. The cable retraction device 1 enclosure is comprised of top cover 33, rear panel 17 and bottom mainframe 16. Rear panel 17 includes a plurality of apertures 48 for cables and tubing to exit the device. Bottom mainframe 16 is captured between the rear panel 17 and the top cover 33 by a plurality of tabs 7. Rear panel 17 and the top cover 33 are secured together by rear panel attachment screws 49. Rubber feet 32 provides table-top grip. Mounting bracket screw boss 54, optionally an integral feature of bottom mainframe 16, provides a mounting point for a pole or wall bracket (not shown) to be attached. Wire retainer 34, optionally an integral feature of bottom mainframe 16, provides a channel to secure cables to avoid chaffing on the rotating spools.

Figure 10:
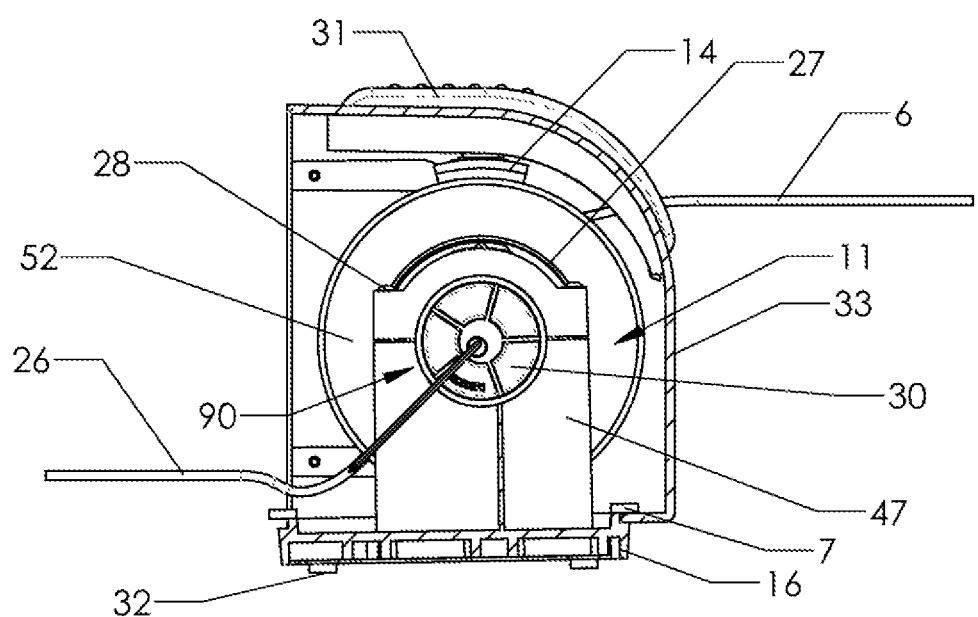
FIG. 10 is a section view taken along the line 10-10 in FIG. 9.
Figure 11:
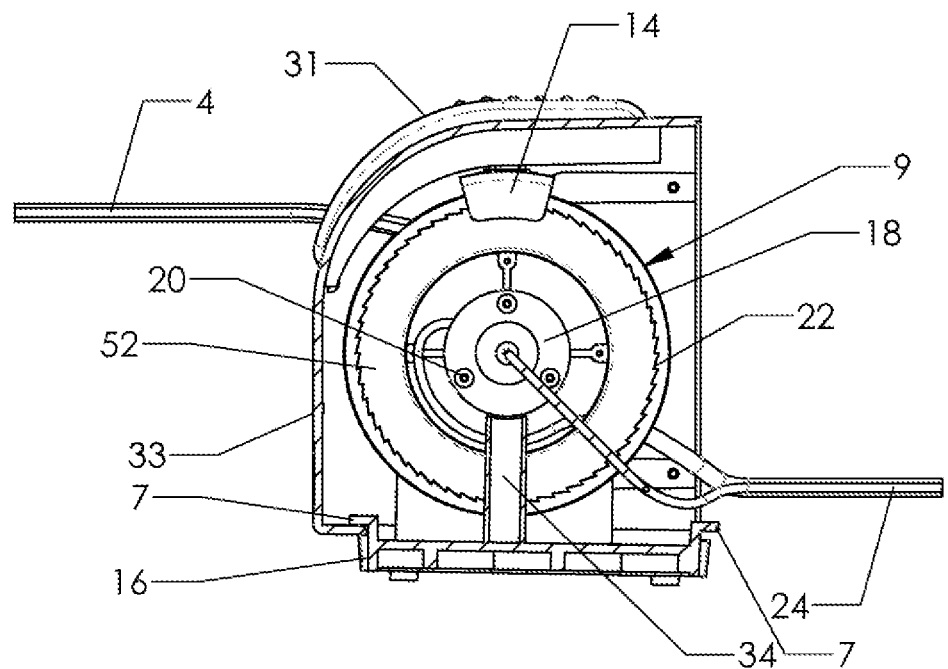
FIG. 11 is a section view taken along the line 11-11 in FIG. 9.
Figure 12:
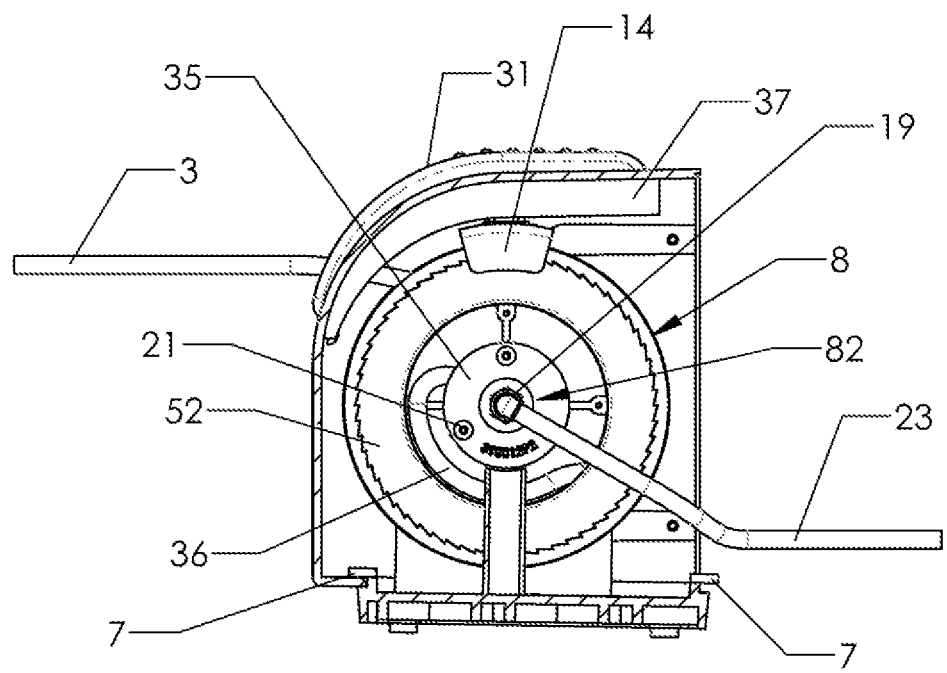
FIG. 12 is a section view taken along the line 12-12 in FIG. 9.
Figure 13:
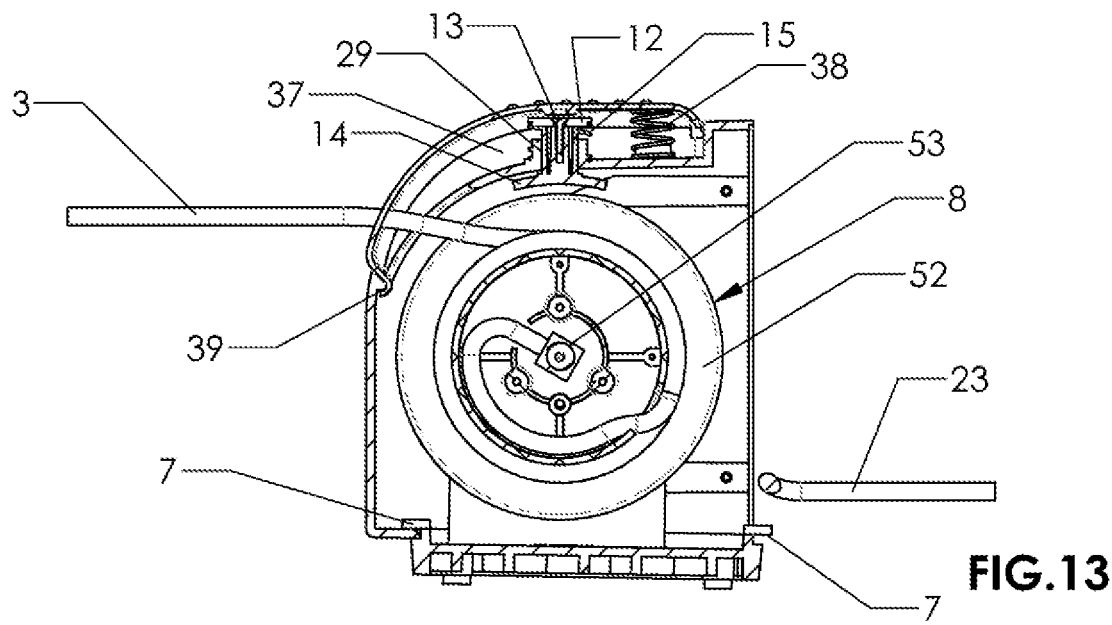
FIG. 13 is a section view taken along the line 13-13 in FIG. 9.
Figure 14:
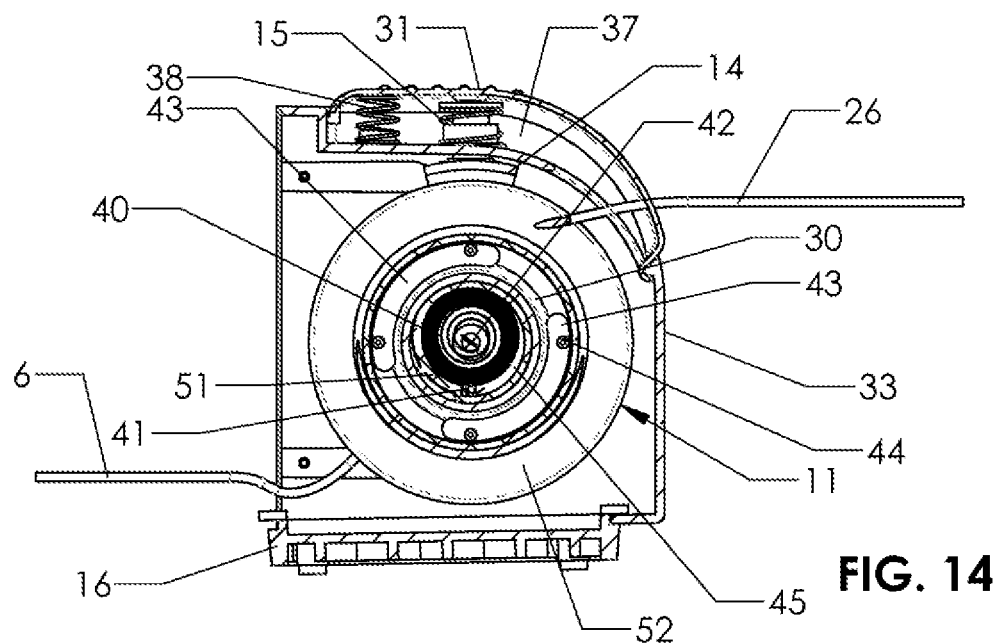
FIG. 14 is a section view taken along the line 14-14 in FIG. 9.
Figure 15:
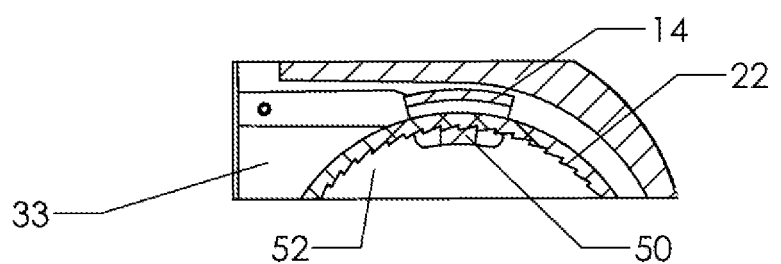
FIG. 15 is a section view taken along the line 15-15 in FIG. 9.
Figure 16:
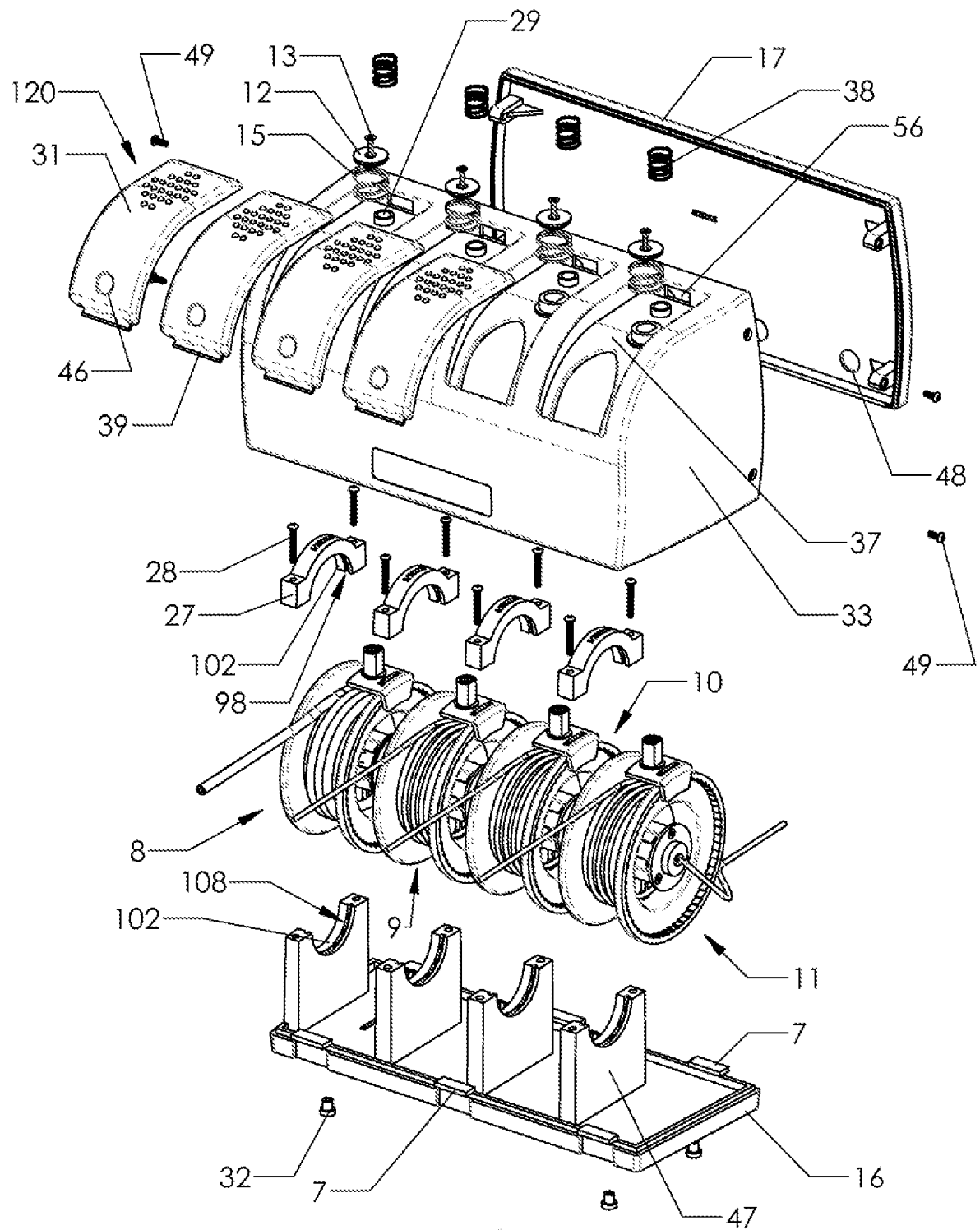

Referring to FIGS. 10 and 16, the blood pressure hose spool assembly 8, the EKG cable spool assembly 9, the oxygen/pulse cable spool assembly 10 and the temperature cable spool assembly 11 are each constrained to the bottom mainframe 16 by a respective axle race clamp 27 capturing an axle race 30 on each of the spool assemblies into a plurality of mainframe cradles 47, optionally an integral feature of bottom mainframe 16, by means of spool axle clamp screw 28. This clamp fixes the axle race 30, thereby all spool assemblies, in all axis and rotation.

Figure 19:
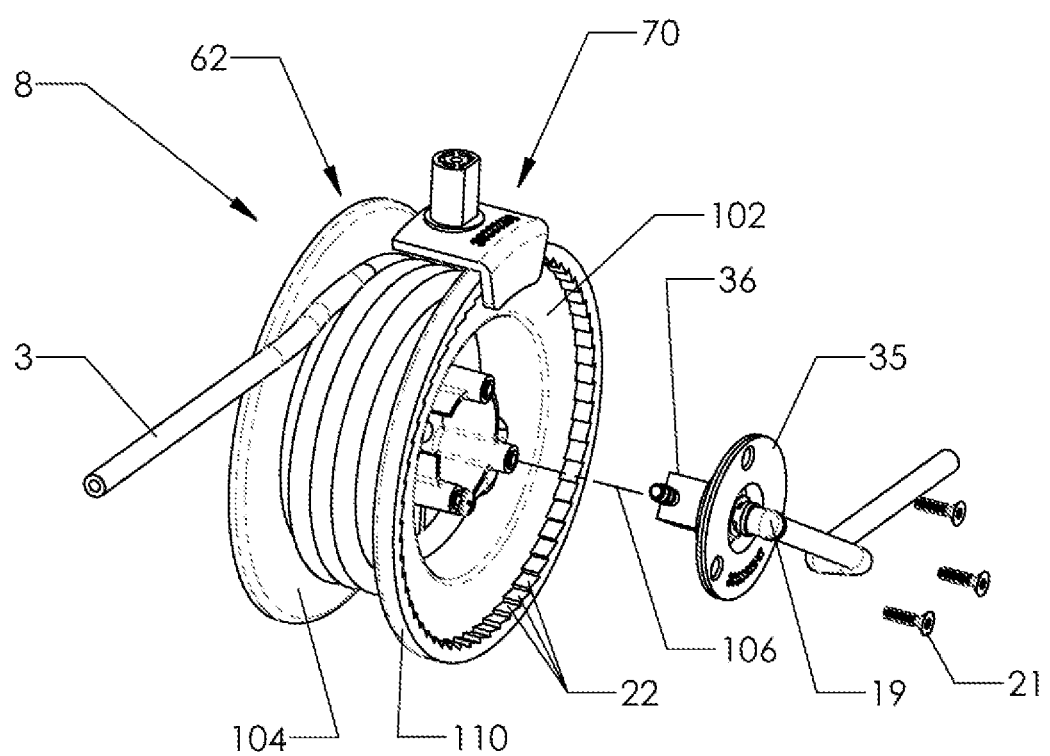
FIG. 19 is an exploded perspective view of a spool assembly having a tube and an air fitting.
Figure 20:
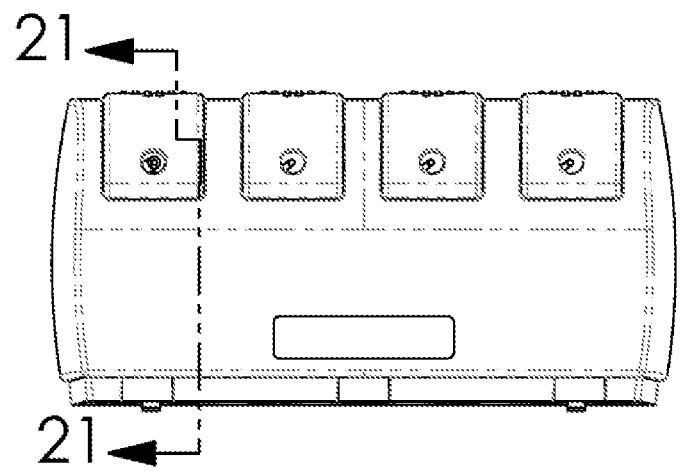
FIG. 20 is another front view of the cable retract system of FIG. 1.
Figure 21:
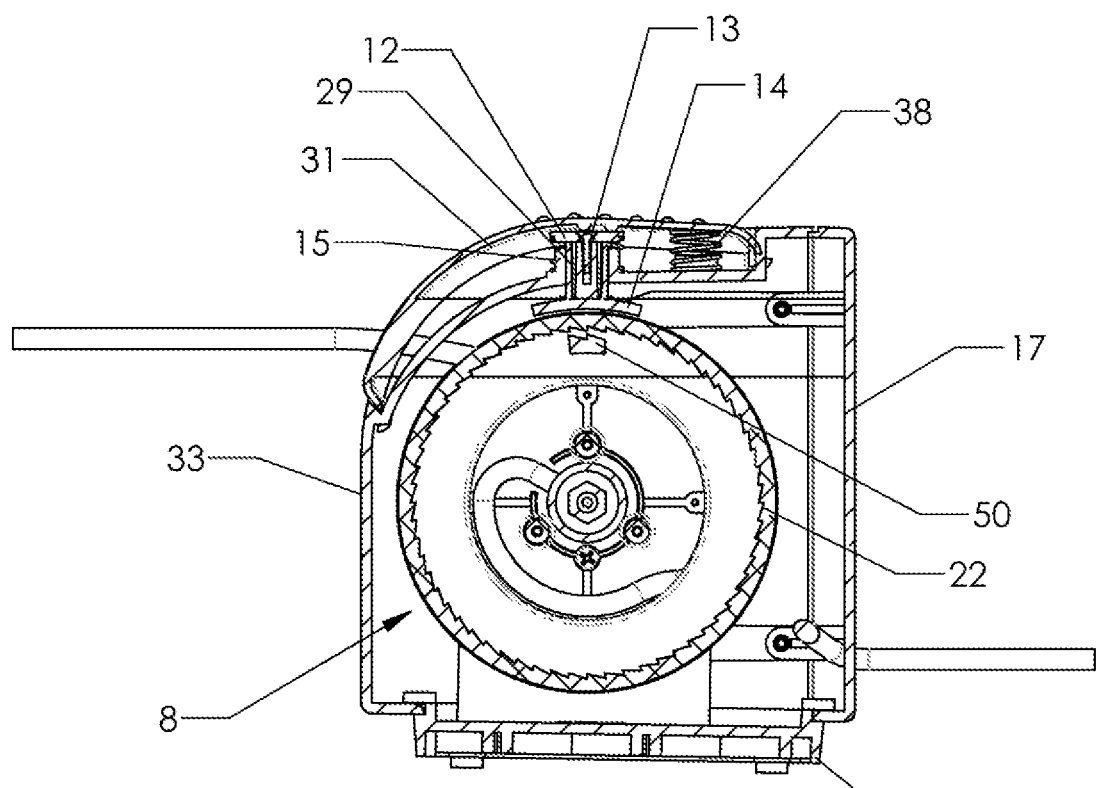
FIG. 21 is a section view taken along the line 21-21 in FIG. 20.

Referring to FIGS. 14, 17, 18 and 19, cable retraction device 1 contains a plurality of spool assemblies, each similarly consisting of a spool 52, spool axle 51, optionally an integral part of spool 52, a constant force rotary spring 40 and an axle race 30. As the spool rotates due to tube or cable extraction, the constant force rotary spring 40, located in spring well 45, optionally an integral part of spool 52, creates a rotary spring bias between the spool 52 and the axle race 30 required to retract the cable or tube. Rotary spring retainer screw 41 secures the constant force rotary spring 40 to spool 52. The wound end of the spring is engaged and wound by spring winder 42 constrained in axle race 30 by spring winder screw 53. Axle race 30 is retained to the spool 52 by two axle race retainers 43 constrained by axle race retainer screws 44. A slip-ring assembly 18 is constrained to the center axis of spool 52 by slip-ring retainer screws 20. Referring to FIG. 19, in the case of the blood pressure hose spool assembly 8, an air fitting 36 and air rotary joint fitting 19 are constrained to the center axis of the spool 52 by the air rotary joint plate 35 and air rotary joint plate retainer screws 21.

Referring to FIGS. 3, 9, 11, 12, 13, 14, 15, 20 and 21, the blood pressure hose spool assembly 8, the EKG cable spool assembly 9, the oxygen/pulse cable spool assembly 10 and the temperature cable spool assembly 11 are all locked in the fully extended position by an identical mechanism consisting of a spool release plunger 14 with integral ratchet teeth 50. Ratchet teeth 50 engage with spool locking teeth 22, optionally an integral feature of spool 52. Ratchet teeth 50 are biased into locking teeth 22 by spool release spring 15 biased between the top cover 33 and the spool release spring retainer 12. Spool release spring retainer 12 is connected to the spool release plunger 14 by means of a spool release spring retainer screw 13. Spring bias is translated by the spool release plunger 14 through the release plunger aperture 29, optionally an integral feature of top cover 33, and onto the locking ratchet teeth 50. As the cable or tube is extracted, the bias is overcome, and the spools are free to rotate. The geometry of the tooth disables the spool from rotating in the opposite direction. To free the spool and allow retraction of the cables or tubing, the release plunger 14 is depressed by means of release lever 31 thereby disengaging ratchet teeth 50 from the locking teeth 22 on spool 52. Release lever 31 is captured by the release lever pivot 39, optionally an integral feature of top cover 33, on the distal end and snapped into the release lever tab aperture 56, optionally an integral feature of top cover 33, by means of release lever tab 55, optionally an integral feature of release lever 31, on the proximal end. The release lever 31 is biased by release lever spring 38 and top cover 33, fully unengaged. To engage release lever 31, thereby depressing release plunger 14 to release the spool, the release lever 31 is pushed into the release lever well 37, optionally an integral feature of top cover 33. Spool release lever aperture 46, integral feature of release lever 31, allows entry of the cables or tubes onto the spools.

Referring to FIGS. 1, 2, 7, 12 and 19, the blood pressure cuff tube 3 is wound around blood pressure hose spool assembly 8 though air fitting 36 and air rotary joint fitting 19. The air rotary joint fitting 19 prevents the blood pressure cuff tube 3 from twisting as the blood pressure hose spool assembly 8 rotates. The blood pressure cuff tube 3 is connected to the vital signs monitor 2 by means of the blood pressure monitor tube 23 that connects to the air rotary joint fitting 19, then passing through the corresponding rear panel aperture 48 on rear panel 17 and connecting to the vital signs monitor 2.

Referring to FIGS. 1, 2, 3, 7, 16, 17 and 18, the EKG harness cable 4, oxygen pulse sensor cable 5 and temperature sensor cable 6 is wound around the corresponding EKG cable spool assembly 9 oxygen/pulse cable spool assembly 10 and temperature cable spool assembly 11 are wound around their corresponding spool assemblies. Each cable connects to an electrically conducting slip ring assembly 18. The slip ring assemblies 18 prevents the cables from twisting as the spool assemblies rotate. The cables are connected to the vital signs monitor 2 by means of the EKG monitor cable 24, the oxygen/pulse monitor cable 25 and the temperature monitor cable 26 that connects to the corresponding slip-ring assemblies 18. The cables pass through the corresponding rear panel apertures 48 on rear panel 17 and then connected to the vital signs monitor 2.

In accordance with the preceding descriptions, the cable retraction device 1 defines least one embodiment of a spooled line handling system having multiple spool assemblies 8, 9, 10, 11 spaced along a common axis 60 (FIG. 3), and a mainframe 16 at least on which the spool assemblies are mounted. Each one of the multiple spool assemblies 8, 9, 10, 11 includes a respective flexible line, with reference at least to the illustrated and non-limiting examples: blood pressure cuff tube 3; EKG harness cable 4; oxygen/pulse sensor cable 5; and temperature sensor cable 6. Each one of the multiple spool assemblies 8, 9, 10, 11 further includes a spool rotationally biased by a spring torque, with reference to the illustrated spool 62 (FIG. 19) with respect to the spool assembly 8, and with reference to the illustrated spool 64 (FIG. 17) with respect to the spool assemblies 9, 10, and 11.

The respective flexible line 3, 4, 5, 6 is mounted on each spool 62, 64, 64, 64 in a variably wound condition such that, as the respective flexible line is extended by unwinding from the spool, the spool is rotated in a first rotational direction 66 (FIG. 3) against the spring torque around the common axis 60 of the multiple spool assemblies. A respective stop device 70 is coupled to each spool selectively preventing rotation of the spool in a second rotational direction 68 (FIG. 3) opposite the first rotational direction 66 thereby selectively preventing, by opposing the spring torque, retraction of the respective flexible line by winding onto the spool.

Each one of the multiple spool assemblies 8, 9, 10, 11 includes a respective release device, with reference at least to the illustrated release levers 31, movably attached directly or indirectly to the mainframe and operatively coupled to the stop device 70. Upon user action on the release device, the release device selectively releases the stop device 70 to allow the spool to rotate in the second rotational direction 68 by the spring torque thereby selectively permitting retraction of the respective flexible line by rewinding at least a portion thereof onto the spool.

In use, a user such as a medical professional manually pulls on any selected flexible line to extend the line. When the extended portion of the flexible line is to be returned to its spool assembly, the user can press on the release lever 31, defining user action thereon, permitting retraction of the respective flexible line.

Figure 3:
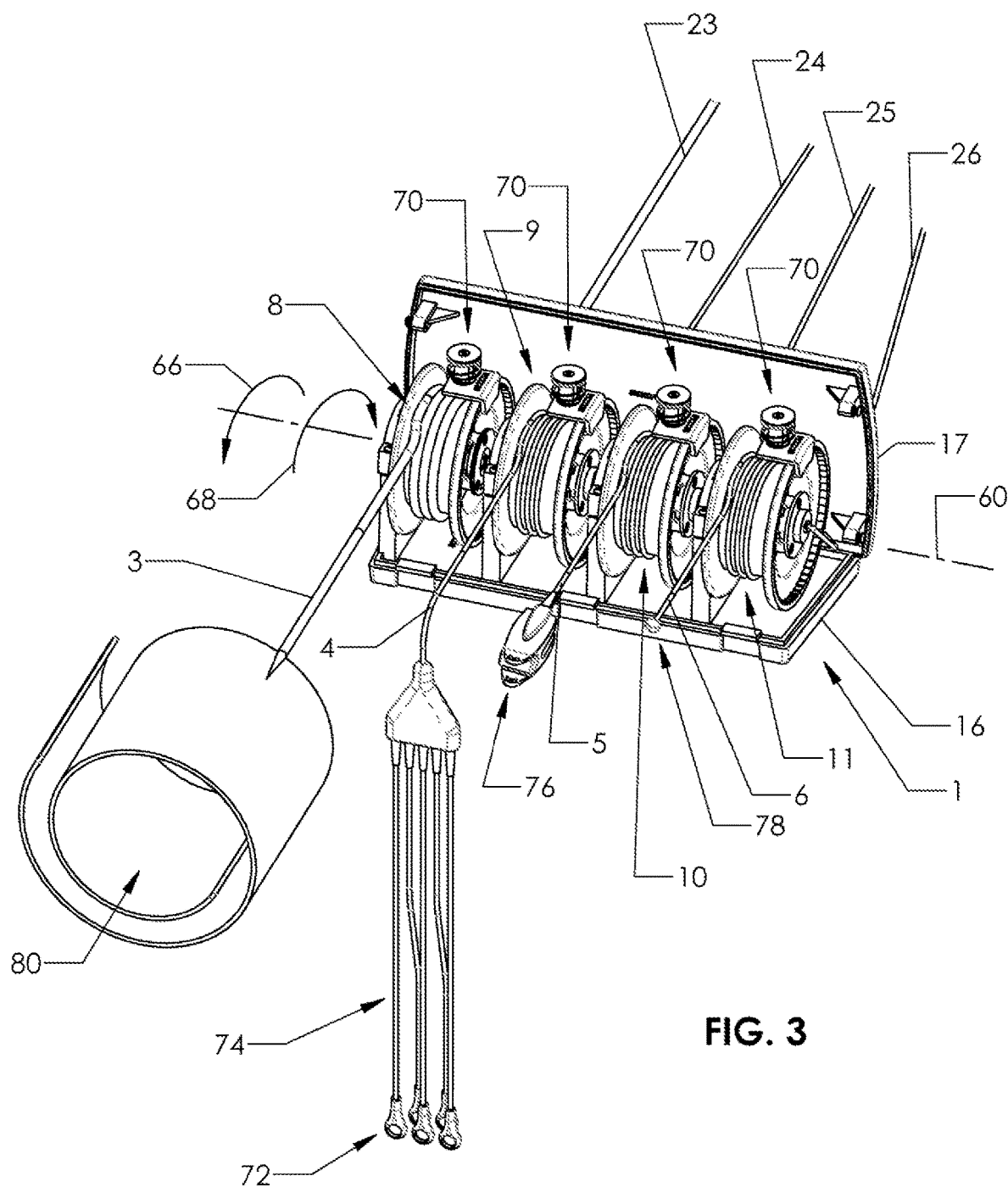
FIG. 3 is an enlarged detail view of a portion FIG. 2.
Figure 4:
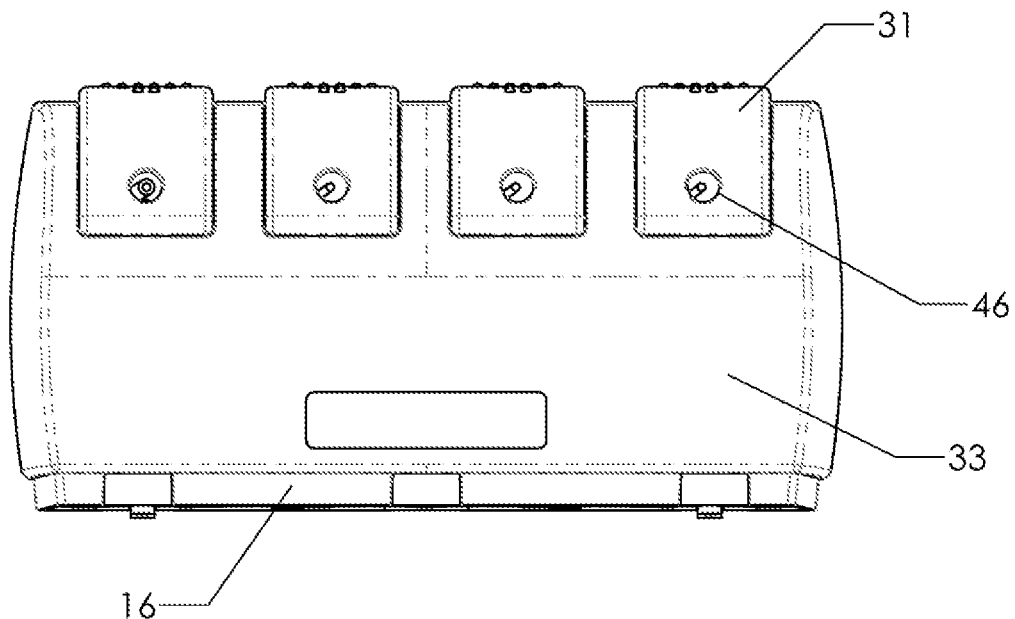
FIG. 4 is a front view of the cable retract system of FIG. 1.
Figure 5:
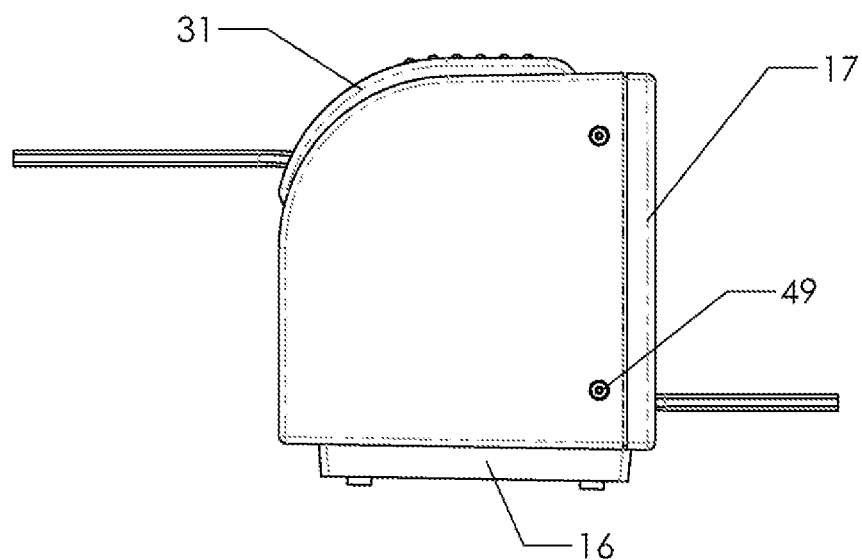
FIG. 5 is a side view of the cable retract system of FIG. 1.
Figure 6:
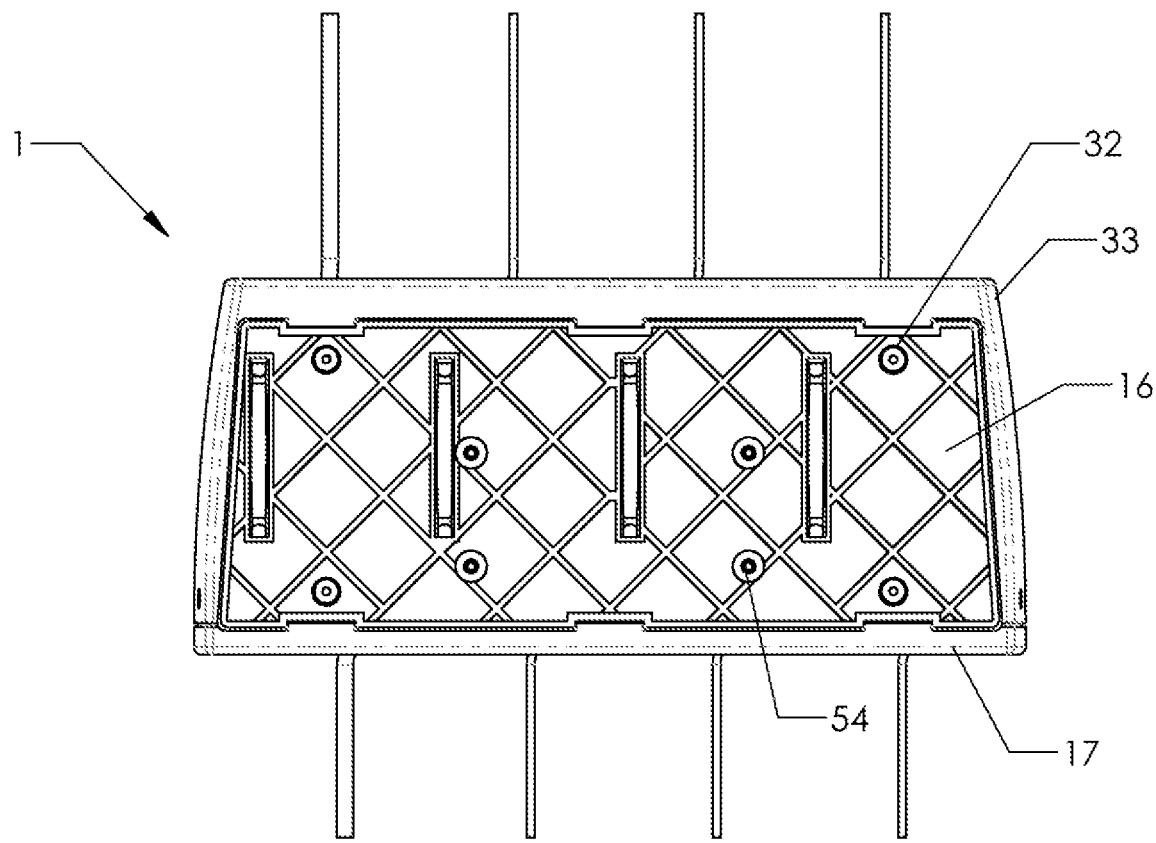
FIG. 6 is a bottom view of the cable retract system of FIG. 1.
Figure 7:
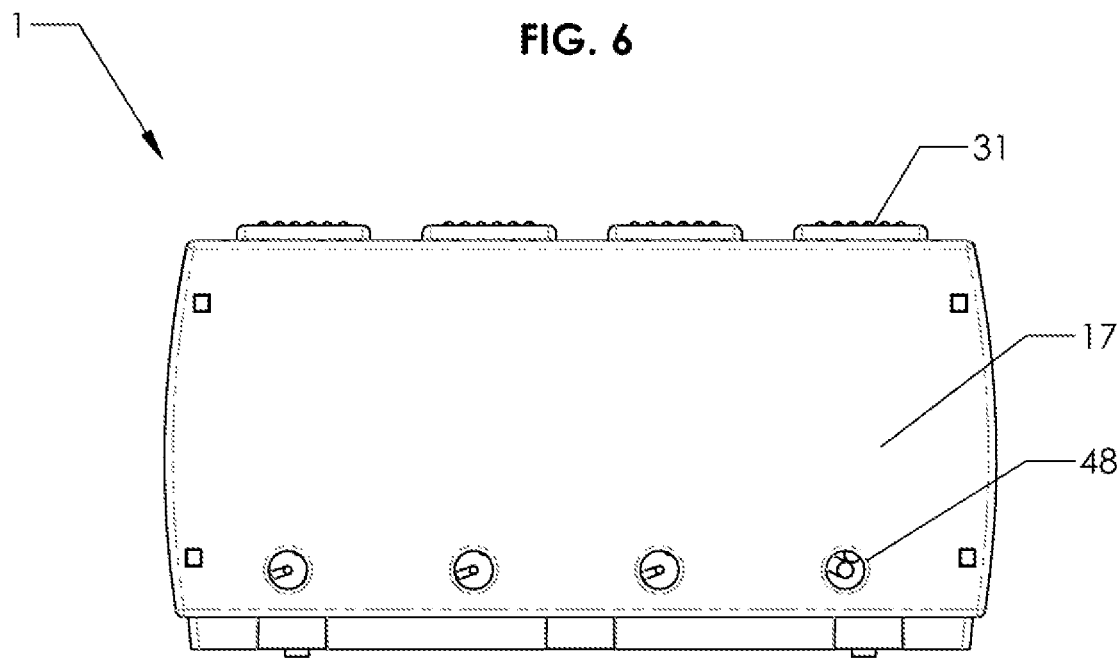
FIG. 7 is a back view of the cable retract system of FIG. 1.
Figure 8:
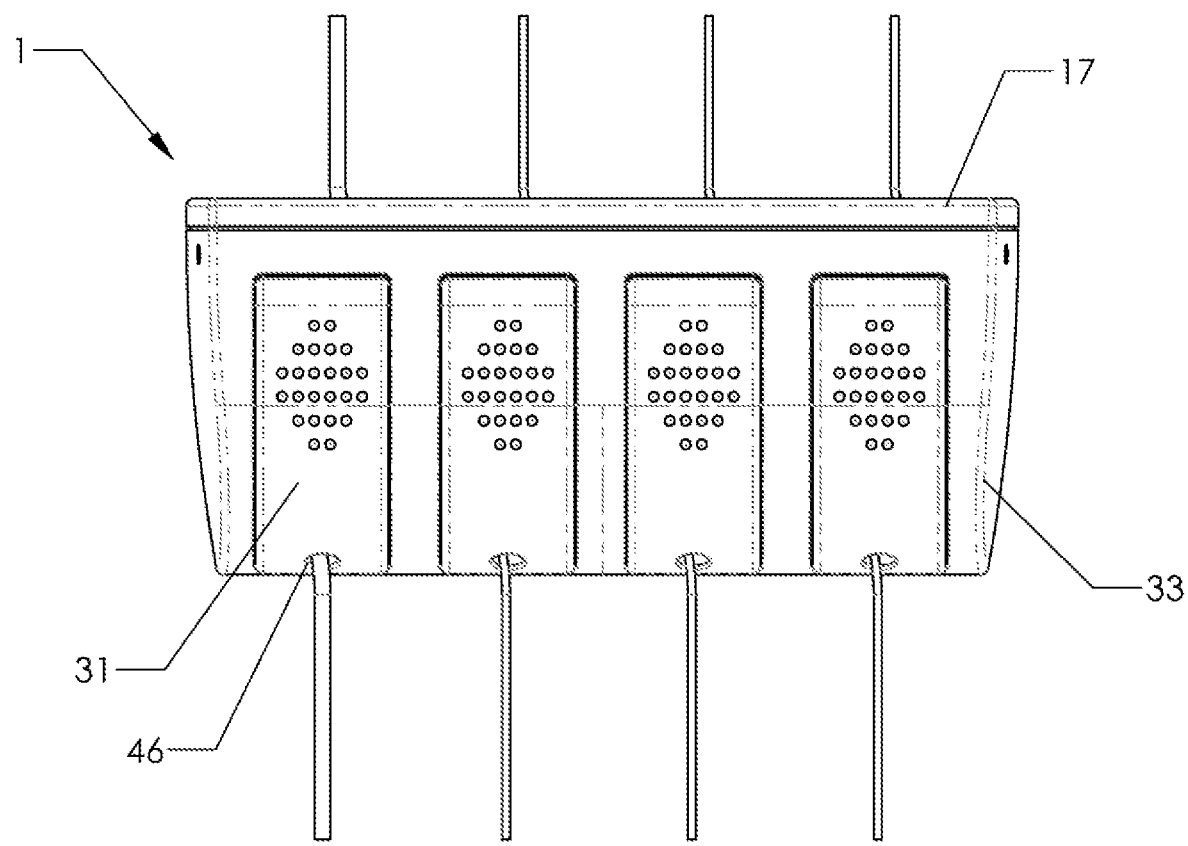
FIG. 8 is a top view of the cable retract system of FIG. 1.
Figure 9:
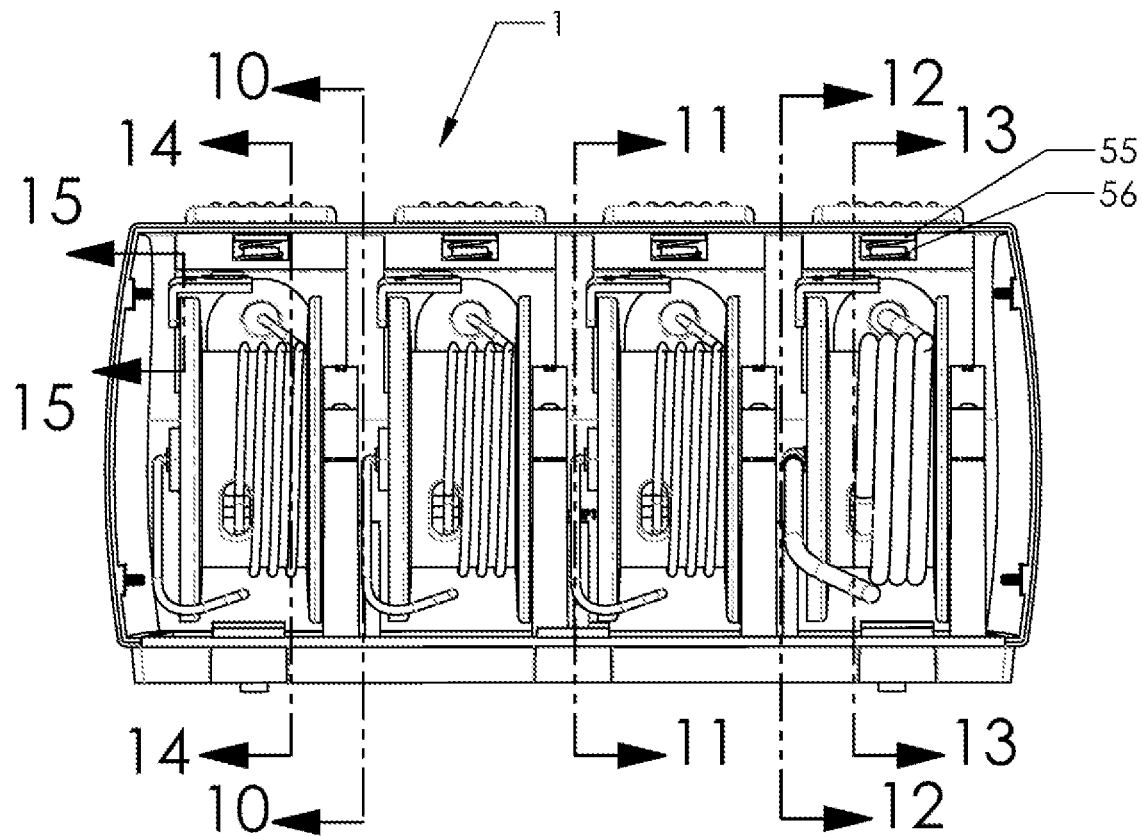
FIG. 9 is a rear view of the cable retract system of FIG. 1 with the cover removed.

In the illustrated embodiment of the spooled line handling system, the respective flexible line of at least one of said multiple spool assemblies comprises a cable comprising at least one electrically conducting wire, with reference at least to the respective flexible lines 4, 5, 6 of the spool assemblies 9, 10, and 11. As represented in FIG. 3, the system can include or can be coupled to at least one sensor connected to the at least one electrically conducting wire. In the illustrated example (FIG. 3), each flexible line 4, 5, 6 includes an electrically conducting signal wire for a respective sensor. In particular: the flexible line 4 is illustrated as an EKG harness cable from which multiple EKG pad sensors 72 extend on respective cables 74 (FIG. 3); the flexible line 5 is illustrated as connected to an oxygen/pulse sensor 76; and the flexible line 6 is illustrated as connected to a temperature sensor 78.

In the illustrated embodiment of the spooled line handling system, the respective flexible line of at least one of said multiple spool assemblies comprises a tube having an interior lumen for fluid passage, with reference at least to the flexible line 3 of the spool assembly 8, which is connected to a blood pressure cuff 80. The flexible line 3 defines an air pressure tube having a lumen for air passage. A rotary air joint 82 (FIG. 11) is connected to the tube opposite the blood pressure cuff 80. The air fitting 36 has a first end coupled to the tube 3 via the rotary air joint 82 and a second end coupled directly or indirectly to a vital signs monitor 2 (FIG. 1).

For each one of the multiple spool assemblies, a non-rotating axle race 30 is affixed to the main frame and retained by the spool. Friction between the spool and the axle race opposes the spring torque thereby damping the rotational speed of the spool at least when the spool rotates in the second rotational direction by the spring torque. Thus the flexible line is returned to the spool by rewinding in a gradual return, preventing damage. In a non-limiting example, the axle race is made of polypropylene plastic. Other durable and smooth materials are within the scope of there descriptions.

Figure 17:
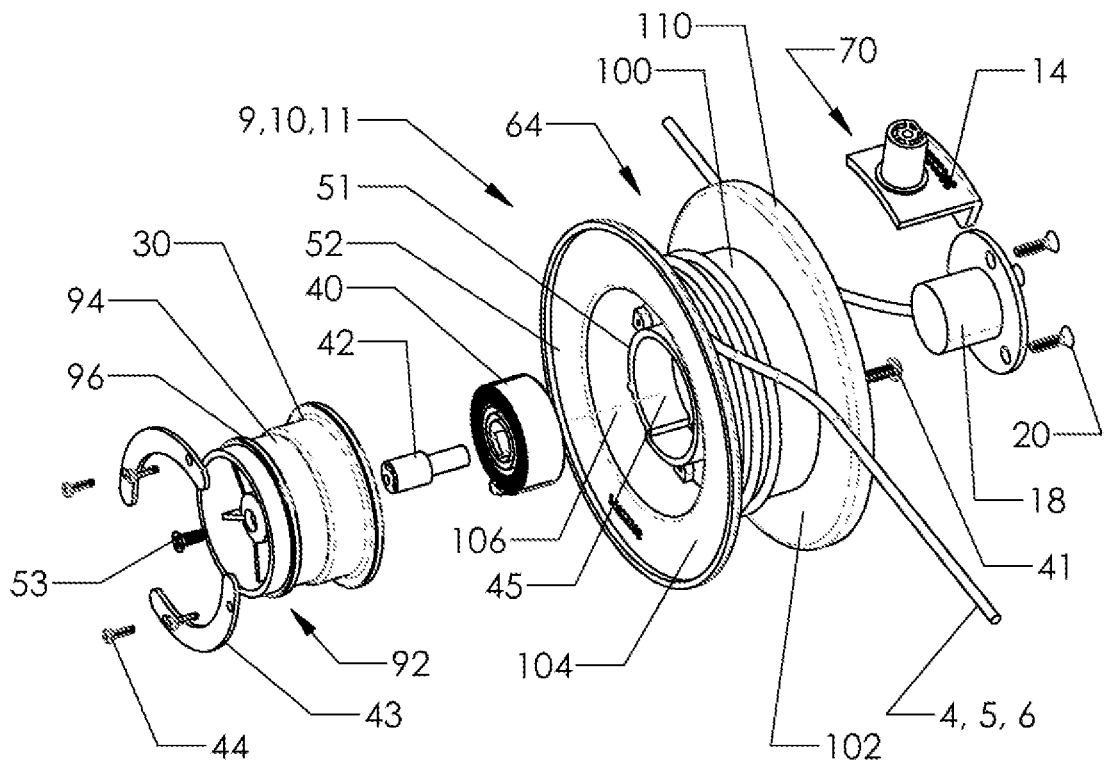
FIG. 17 is an exploded perspective view of a spool assembly, according to at least one embodiment.
Figure 18:
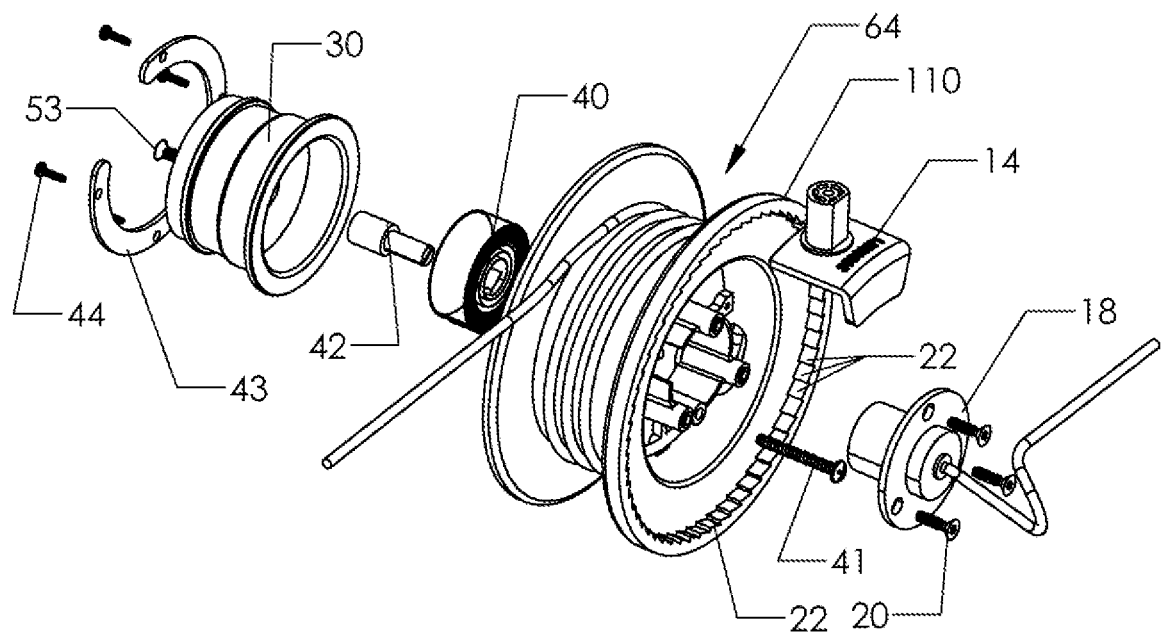
FIG. 18 is an exploded view of the spool assembly of FIG. 17 from another perspective.

Each non-rotating cradle 47 is connected to the mainframe 16 and supports a respective spool assembly. A respective non-rotating clamp 27 is connected at least in part to each cradle 47 by at least one fastener, illustrated as a screw 28 (FIG. 10, 16). The cradle 47 and clamp 27 together define a capture hole 90 (FIG. 10) in which an engagement portion 92 of the axle race 30 is fixedly captured thereby affixing the axle race 30 to the main frame 16. The spool 64 rotates relative to the axle race 30 when the spool is rotated. The engagement portion 92 of the axle race 30 comprises a radially outward facing cylindrical portion 94 and a registration ring 96 (FIG. 17). The cradle 47 and clamp 27 each define a respective radially inward facing arcuate wall (FIG. 16). The arcuate wall 102 of the cradle 47 and the arcuate wall 104 of the clamp 27 together define the capture hole 90 (FIG. 10), and each defines a respective arcuate groove. The arcuate groove 98 of the clamp 27 and the arcuate groove 108 of the cradle 47 together define a registration groove in which the registration ring 96 (FIG. 17) is captured.

Each of the multiple spool assemblies 8, 9, 10, 11 includes a spring, illustrated as a constant force rotary spring 40 (FIG. 17), torsionally coupling the spool 62, 64 to its corresponding axle race 30. The spring provides the spring torque by which the spool to rotates in the second rotational direction 68 (FIG. 3) for retraction of the respective flexible line by rewinding at least a portion thereof onto the spool.

In the illustrated embodiment, each spool 62 (FIG. 19), 64 (FIG. 17) includes a cylinder 100 defining an engagement surface on which the respective flexible line is mounted on the spool in the variably wound condition. A first flange 102 is affixed to a first longitudinal end of the engagement surface of the cylinder 100, and a second flange 104 is affixed to a second longitudinal end of the engagement surface of the cylinder 100. Each flange extends radially outward from the cylinder for maintaining the flexible line on the spool in the variably wound condition. The cylinder of each spool has a center axis 106 coincident with the common axis 60 (FIG. 3) in the assembled condition of the system.

In the illustrated embodiment, each spool 62, 64 includes a ring 110 connected to the first flange 102, and locking teeth 22 extending from an interior of the ring radially inward toward the common axis (106, 60). The locking teeth 22 engage the stop device 70 when the stop device prevents rotation of the spool 62, 64 in the second rotational direction 68. Features of the stop device 70 are described in the preceding descriptions with reference to the spool release plunger 14 with integral ratchet teeth 50. The stop device 70 includes the plunger 14 and attached ratchet teeth 50 (FIG. 15) for engaging the locking teeth 22 of the corresponding spool. The stop device 60 is biased to engage the ratchet teeth 50 with the locking teeth 22.

Features of the release devices 120 (FIG. 16) are described in the preceding descriptions with reference to the illustrated release levers 31. Upon user action on any particular release device 120, the release device moves the stop device 70 thereby disengaging the ratchet teeth 50 from the locking teeth 22. As illustrated each release device comprises the respective pivotable lever 31 having an aperture 46 through which the respective flexible line extends.

In the assembled condition of the system, the cover 33 is attached to the mainframe 16, the mainframe and cover together defining an enclosure in which the multiple spool assemblies 8, 9, 10, 11 are housed. As illustrated, the cover 33 includes, each in one-to-one correspondence with a respective one of the multiple spool assemblies, a lever well 37 at least partially receiving a respective pivotable lever 31. The cover includes a rear panel 17 from which rearward flexible leads extend, each in one-to-one correspondence with a respective one of the multiple flexible lines, to couple the respective flexible lines to a vital signs monitor 2. Rearward flexible leads refer at least to the non-limiting examples (FIG. 1): blood pressure monitor tube 23; EKG monitor cable 24; oxygen/pulse monitor cable 25; and temperature monitor cable 26.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A spooled line handling system comprising:
   multiple spool assemblies spaced along a common axis; and
   a mainframe at least on which the spool assemblies are mounted;
   wherein each one of the multiple spool assemblies comprises:
      a respective flexible line;
      a spool rotationally biased by a spring torque, the respective flexible line mounted on the spool in a variably wound condition such that, as the respective flexible line is extended by unwinding from the spool, the spool is rotated in a first rotational direction against the spring torque around the common axis of the multiple spool assemblies;
      a stop device coupled to the spool selectively preventing rotation of the spool in a second rotational direction opposite the first rotational direction thereby selectively preventing, by opposing the spring torque, retraction of the respective flexible line by winding onto the spool; and
      a release device movably attached to the mainframe and operatively coupled to the stop device, wherein upon user action on the release device, the release device selectively releases the stop device to allow the spool to rotate in the second rotational direction by the spring torque thereby selectively permitting retraction of the respective flexible line by rewinding at least a portion thereof onto the spool.

2. The spooled line handling system according to claim 1, wherein:
   the respective flexible line of at least one of said multiple spool assemblies comprises a cable comprising at least one electrically conducting wire; and
   the respective flexible line of at least one other of said multiple spool assemblies comprises a tube.

3. The spooled line handling system according to claim 2, further comprising at least one sensor connected to the at least one electrically conducting wire, the sensor comprising at least one of an EKG pad, an oxygen sensor, a pulse sensor, and a temperature sensor.

4. The spooled line handling system according to claim 3, wherein the at least one electrically conducting wire is further electrically coupled to a vital signs monitor via an electrically conducting slip ring assembly.

5. The spooled line handling system according to claim 3, further comprising a blood pressure cuff connected to the tube.

6. The spooled line handling system according to claim 5, further comprising:
   a rotary air joint connected to the tube opposite the blood pressure cuff; and
   an air fitting having a first end coupled to the tube via the rotary air joint and a second end coupled directly or indirectly to a vital signs monitor.

7. The spooled line handling system according to claim 1, wherein each one of the multiple spool assemblies further comprises a non-rotating axle race affixed to the main frame and retained by the spool.

8. The spooled line handling system according to claim 7, wherein a friction between the spool and the axle race opposes the spring torque thereby damping a rotational speed of the spool at least when the spool rotates in the second rotational direction by the spring torque.

9. The spooled line handling system according to claim 7, further comprising, each in one-to-one correspondence with a respective one of the multiple spool assemblies:
   a non-rotating cradle connected to the mainframe; and
   a non-rotating clamp connected at least in part to the cradle by at least one fastener, wherein the cradle and clamp together define a capture hole in which an engagement portion of the axle race is fixedly captured thereby affixing the axle race to the main frame, and
   wherein the spool rotates relative to the axle race when the spool is rotated.

10. The spooled line handling system according to claim 9, wherein:
    the engagement portion of the axle race comprises a radially outward facing cylindrical portion and a registration ring;
    the cradle and clamp each define a respective radially inward facing arcuate wall, the arcuate wall of the cradle and arcuate wall of the clamp together defining the capture hole;
    the arcuate wall of the cradle and arcuate wall of the clamp each define a respective arcuate groove; and
    the arcuate groove of the clamp and the arcuate groove of the cradle together define a registration groove in which the registration ring is captured.

11. The spooled line handling system according to claim 1, wherein each one of the multiple spool assemblies comprises a spring torsionally coupling the spool to the axle race, the spring providing said spring torque.

12. The spooled line handling system according to claim 1, wherein each spool further comprises:
    a cylinder defining an engagement surface on which the respective flexible line is mounted on the spool in the variably wound condition; and
    a first flange affixed to the cylinder and extending radially outward from the cylinder for maintaining the flexible line on the spool in the variably wound condition,
    wherein the cylinder of each spool has a center axis defined by the common axis.

13. The spooled line handling system according to claim 12, wherein each spool further comprises:
    a ring connected to the first flange; and
    locking teeth extending from the ring radially inward toward the common axis, the locking teeth engaging the stop device when the stop device prevents rotation of the spool in the second rotational direction.

14. The spooled line handling system according to claim 13, wherein:
    the stop device comprises ratchet teeth for engaging the locking teeth;
    the stop device is biased to engage the ratchet teeth with the locking teeth; and
    upon user action on the release device, the release device moves the stop device thereby disengaging the ratchet teeth from the locking teeth.

15. The spooled line handling system according to claim 14, wherein the release device comprises a pivotable lever having an aperture through which the respective flexible line extends.

16. The spooled line handling system according to claim 15, further comprising a cover attached to the mainframe, the mainframe and cover together defining an enclosure in which the multiple spool assemblies are housed.

17. The spooled line handling system according to claim 16, wherein the cover comprises, each in one-to-one correspondence with a respective one of the multiple spool assemblies, a lever well at least partially receiving the pivotable lever.

18. The spooled line handling system according to claim 1, wherein the cover comprises a rear panel from which rearward flexible leads extend, each in one-to-one correspondence with a respective one of the multiple spool assemblies, to couple the respective flexible lines to a vital signs monitor.

* * * * *